United States Patent [19]

Bergli et al.

[11] Patent Number: 5,476,793
[45] Date of Patent: Dec. 19, 1995

[54] METHOD FOR DECIDING THE REACTIVITY AND SOOT INDEX OF CARBON PRODUCTS

[75] Inventors: Knut Bergli, Bødalen; Trygve Foosnaes, Årdalstangen; Tormod Naterstad, Asker, all of Norway

[73] Assignee: Norsk Hydro a.s., Oslo, Norway

[21] Appl. No.: 24,316

[22] Filed: Mar. 1, 1993

[30] Foreign Application Priority Data

Feb. 28, 1992 [NO] Norway ..................................... 920789

[51] Int. Cl.⁶ ................................................. G01N 31/12
[52] U.S. Cl. ............................ 436/34; 436/145; 436/160
[58] Field of Search ................................... 436/34, 6, 37, 436/145, 155, 160

[56] References Cited

U.S. PATENT DOCUMENTS 4,051,224  9/1977  Duclaux et al. ..................... 423/210

OTHER PUBLICATIONS

P. J. Rhedey, Light Metals, 1982, pp. 713–725, "Carbon Reactivity and Aluminum Reduction Cell Anodes".
G. J. Houston et al., Light Metals, 1985, pp. 885–899, "Reactivity Testing of Anode Carbon Materials".
T. Müftüoglu et al., Light Metals, 1987, pp. 471–476, "Reactivity and Electrolytic Consumption of Anode Carbon With various Additives".

*Primary Examiner*—Jeffrey R. Snay
*Attorney, Agent, or Firm*—Wenderoth, Lind & Ponack

[57] ABSTRACT

Air reactivity, $CO_2$ and soot index of a carbon product is determined. The air reactivity and $CO_2$ reactivity of a sample of a carbon product are determined on the basis of the same test of the same sample. Air reactivity is analyzed first and, when such analysis is finished, $CO_2$ reactivity is automatically analyzed on the same sample. The soot index is determined by collecting and weighing soot dust. A vertical tube furnace includes an inlet for the introduction of gas, and a sample holder which is freely suspended from a weighing device and extends down into the tube furnace. The sample holder is provided with one or more thermocouples for registering temperature of a carbon product.

7 Claims, 6 Drawing Sheets

5,476,793

METHOD FOR DECIDING THE REACTIVITY AND SOOT INDEX OF CARBON PRODUCTS

BACKGROUND OF THE INVENTION

The present invention relates to a new method for deciding the reactivity and soot index of carbon products such as granular coke and baked or burned carbon core samples, and to equipment therefor.

Everyone involved in traditional aluminum production knows full well that some of the anode material of production equipment takes part in reactions which do not benefit the production of metal. The most obvious aspect is the corrosion of the top of the anode where it comes into contact with the air. In a more concealed manner, mainly on the underside of the anode, another unfortunate process takes place. Here some of the $CO_2$ gas from the primary reaction reacts with the carbon of the anode to form CO, carbon monoxide. According to P. J. Rhedey, Alcan International Limited, Kingston Laboratories, in "Carbon reactivity and aluminum reduction cell anodes", the reaction with air and the reaction with $CO_2$ contribute to a significant part of consumption of the anode. The reactions with air and $CO_2$ can, furthermore, cause the anode material to crumble, which causes operational problems with anode particles in the electrolyte, so-called sooting.

From these facts it is not difficult to understand that, for both the anode producer and the user, it is necessary to be able to predict some of the tendency of the anode to react with air and with carbon dioxide.

The reactivity of anodes can be measured in a number of ways, depending on how it is chosen to attack the problem. In general terms, regardless of the manner of attack, such a method must be at least:

selective, sufficiently sensitive, sufficiently reproducible.

A selective method is a method which mainly reacts to the properties of the anode which are of importance for the air/$CO_2$ reactions under operating conditions. Satisfactory sensitivity can be defined as the ability to reveal changes in the stated properties at a level at which this would be of significance for the operation of electrolysis cells of the production equipment. Reproducibility, i.e. the distribution of results from tests on several samples from the same anode, should not be so large that it is of real significance in the assessment of the anode's user properties. This is the same as saying that, regardless of how many times a piece of carbon is tested, the conclusion with regard to its quality must remain the same.

In the method of analysis which forms the object of the present invention, instead of scaling down operating conditions in electrolysis cells to manageable laboratory size, emphasis is placed on developing a reproducible test which can be employed to carry out quality grading of anodes. In addition, the point of departure for the grading is the hypothesis that the lowest possible reactivity and sooting are desirable.

The tendency of an anode to react, i.e. how rapidly the reaction takes place, has been designated "reactivity". Thus, there are two types of reactivity, namely $CO_2$ reactivity and air reactivity. Both reactions lead to a gasification of a sample, i.e. it loses weight. By registering this loss of weight, it is possible to obtain a measurement of the reactivity.

Sooting is caused in this connection by the reactivity being different in the aggregate and the binding agent of the anode material. If the binding coke, for example, reacts least, this will cause the particles in the aggregate to be undermined and gradually to fall out during the test (and under operating conditions). After the sample has been exposed to the reactant gas over a certain period of time, it is brushed and all the loose material is collected and weighed. This is thus soot in the context of the analysis. It has been chosen to express the level of sooting as the ratio of the weight of the soot and the overall loss in weight, where the overall loss of weight is the total weight of the gasified part and the part brushed off.

The reactivities are determined by means of a regression analysis for the last 30 minutes of reaction time. The following formulae apply.

$$\text{Reactivity} = \frac{G_{30}}{\pi * C * L * t_{30}}, \text{mg} \times \text{cm}^{-2} \times \text{h}^{-1}$$

$$\text{Soot index} = \frac{100 * S}{S + G}, \%$$

G=gasified (weight loss) during the whole test (max. 190 min.), mg.

$G_{30}$=gasified (weight loss) during the last 30 min., mg.

S=soot formed with normal test length (max. 190 min.), mg.

D=sample diameter, cm.

L=sample length, cm.

$t_{30}$=½ hour.

In the test methods for deciding air and $CO_2$ reactivity which have been known up to now, at least two independent tests must be carried out, one to decide the air reactivity and another to decide the $CO_2$ reactivity.

SUMMARY OF THE INVENTION

The present invention thus relates to a method for deciding the air and $CO_2$ reactivity of a sample of a carbon product in one and the same test. The soot index can also be determined on the basis of this test.

This method is very time-saving in relation to existing techniques in which air and $CO_2$ reactivity have to be decided from separate tests. Time is saved both because it is only necessary to prepare and handle one sample to carry out an analysis of both air and $CO_2$ reactivity and because only one heating and cooling period is necessary. In addition, less manpower is required to carry out this analysis than in existing techniques. This then has the result that the method in accordance with the invention is more economical than existing techniques.

Contrary to existing techniques, the analysis of $CO_2$ reactivity using the procedure in accordance with the invention will be a study of a pre-oxidized sample, as the sample will already have been exposed to air during the air reactivity analysis. This is an advantageous aspect of the invention because the $CO_2$ reactivity measured on a pre-oxidized sample will be more in accordance with real conditions in electrolysis cells.

The method in accordance with the invention is characterized in that the air and $CO_2$ reactivity of a sample of a carbon product are decided from the same test, first by analyzing the air reactivity and, when such analysis is complete, automatically analyzing the $CO_2$ reactivity on the same sample. Finally, the soot index is decided by collecting and weighing the soot dust from the sample. Preferred features of this method are to analyze the air reactivity at 525° C. and the $CO_2$ reactivity at 960° C.

The reaction between the $CO_2$ and the carbon is endothermic, whereas the air reaction, which is normal combustion, is exothermic. Both are strongly dependent on temperature. This phenomenon creates a dilemma in choosing the test temperature. On the one hand, the test should take place at temperatures close to those found in the electrolysis cells in order not to miss out on the factors which are important for reactivity and sooting. It has, for example, been demonstrated that several elements and compounds can occur as accelerators and inhibitors in these reactions, however, the effect is dependent on temperature. On the other hand, this must be weighed against the possibilities for designing equipment and a practicable method for registering what happens. In this procedure, a compromise has been made by carrying out the $CO_2$ test at 960° C. and the air test at 525° C. This is the most practical method, even if these temperatures are somewhat lower than the temperature in the wear surface of the anode, the top and shoulders respectively, of which they are to provide a convincing representation.

The present invention also relates to equipment for carrying out the above-mentioned method. Such equipment is characterized by a vertical tube furnace with an inlet for the introduction of gas, and a sample holder for the carbon product which is suspended freely from a weighing device and reaches down into the tube furnace. The sample holder is provided with one or more thermocouples for recording the temperature in the carbon product.

BRIEF DESCRIPTION OF THE DRAWINGS

Other objects, features and advantages of the invention will be apparent from the following detailed description taken with the accompanying drawings, wherein.

DETAILED DESCRIPTION OF THE INVENTION

Figure 1:
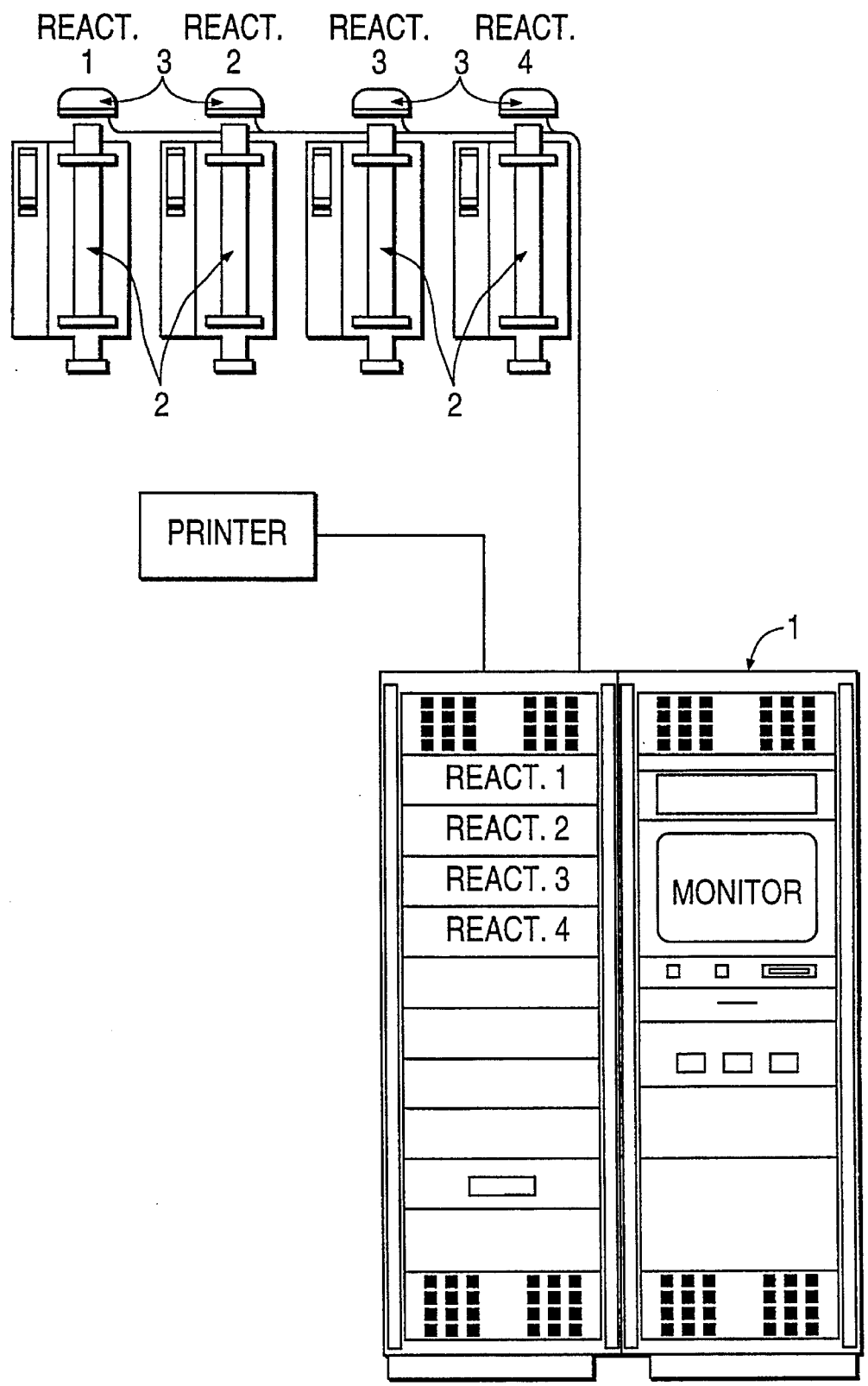
FIG. 1 is a schematic view illustrating an apparatus employable for carrying out the method of the invention.
Figure 2:
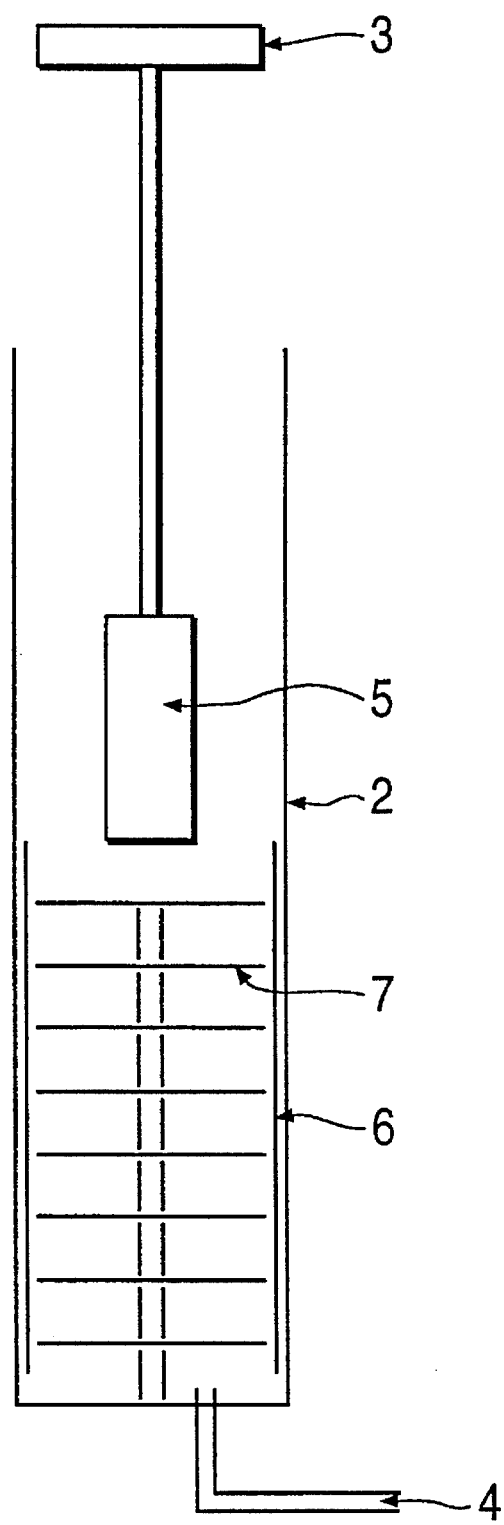
FIG. 2 is an enlarged schematic view of the interior of one tube furnace shown in FIG. 1.

Equipment or apparatus according to the invention is shown in FIGS. 1 and 2 and includes a processing unit 1, vertical tube furnaces 2, each including a weighing device 3, inlet 4 for the introduction of gas, sample holder 5, radial radiation shield 6, and heating element 7.

The method comprises the use of computer equipment for process control, data logging and calculation. In principle there is no limit to the number of samples which can be analyzed in parallel by connecting a number of analysis devices to the computer equipment.

The loss of weight of a carbon sample due to gasification by air and carbon dioxide is measured continuously by the processing unit 1 which is connected to the weighing devices 3. Thermocouples of the sample holders are also connected to the processing unit 1 so that the temperature of the samples can be recorded and checked. The temperature in the furnaces 2 and the temperature of the samples are regulated by the processing unit 1.

Figure 3:
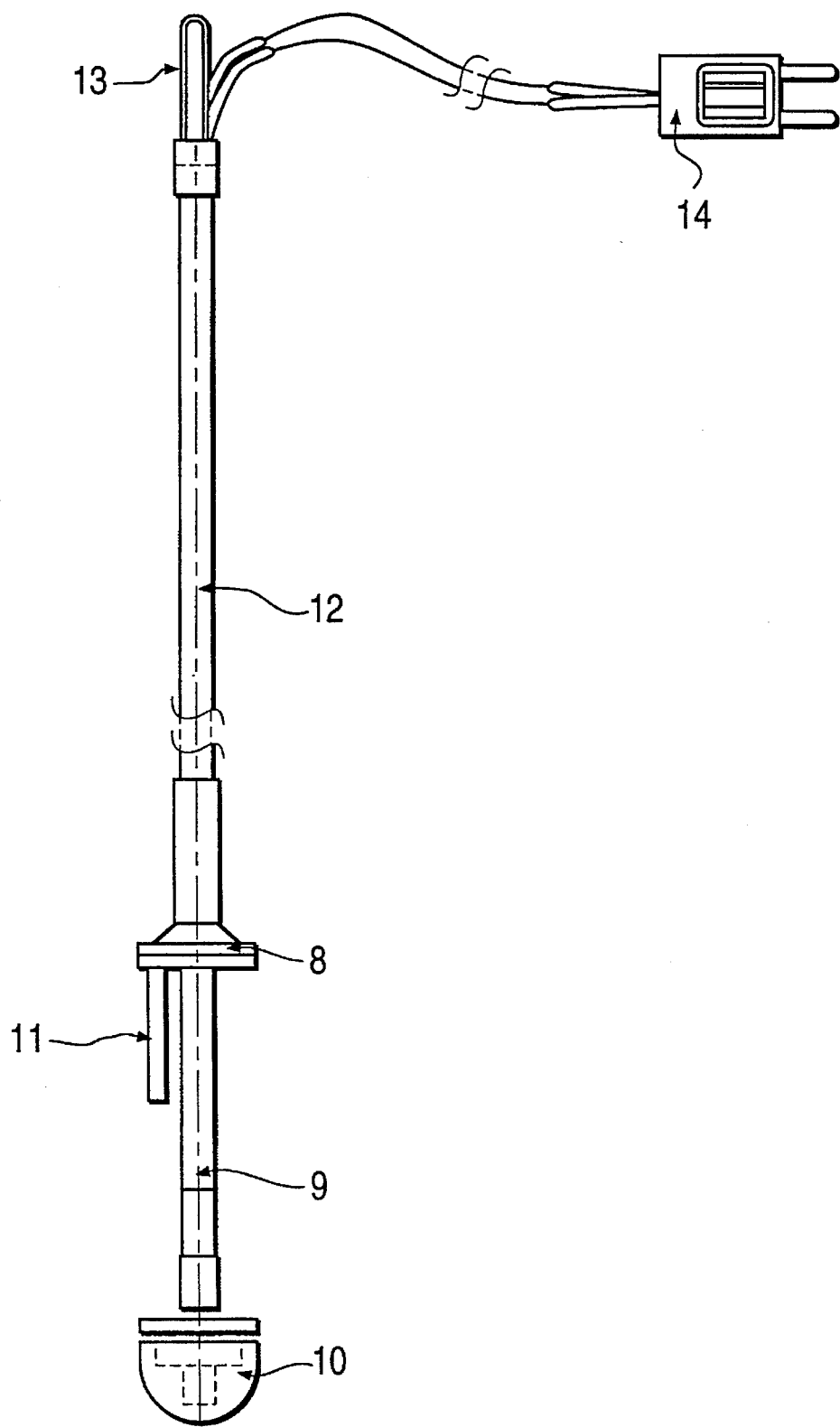
FIG. 3 is an enlarged view of one embodiment of a sample holder employable in a tube furnace.

In the analysis of baked or burned carbon core samples, the sample has the form of a cylinder. The sample holder which is used in this instance is shown in FIG. 3 and comprises a flange 8 on which is fastened a pin 9 that is threaded at a lower end thereof and a thermocouple 11. An end piece 10 has threads complementary to the threads of pin 9 and can be screwed onto pin 9, thereby to fasten a sample which is provided with two holes into which fit the pin 9 and the thermocouple 11. A ceramic pipe 12 is fastened at the top of the flange 8. A top end of pipe 12 is provided with a suspension device 13. Wires of thermocouple 11 extend through pipe 12 to a plug 14.

Only the side or peripheral surface of the cylinder-shaped sample takes part in the reaction. The end surfaces are not exposed because they are covered by flange 8 and end piece 10. The reactant gas flows in laminar flow upwardly along the sample to create identical reaction conditions over the entire surface thereof. It is important that the temperature be kept constant over the entire reaction surface.

Figure 4:
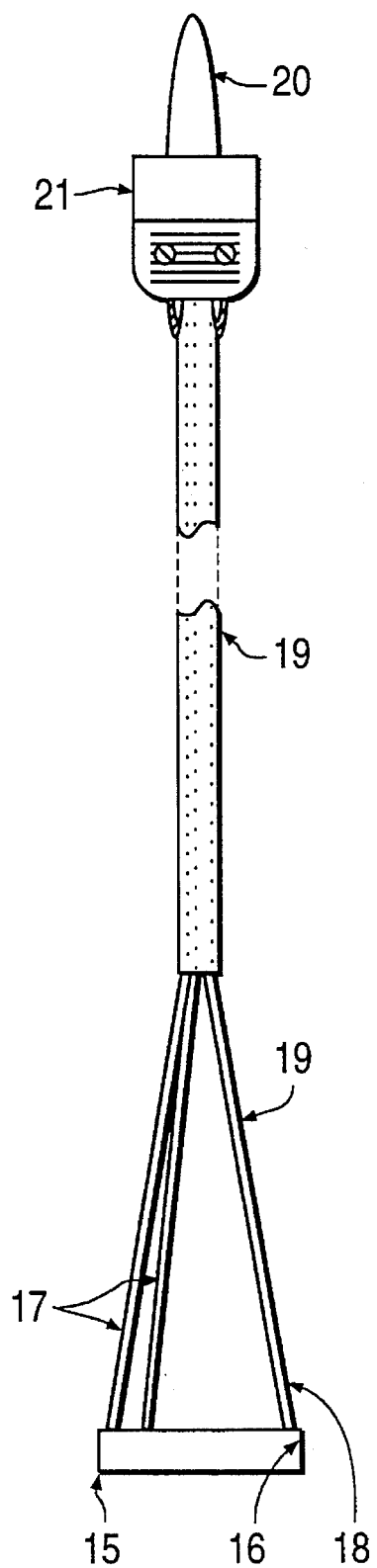
FIG. 4 is an enlarged view of another embodiment of a sample holder.

In the analysis of granular carbon products, e.g. granular coke, another sample holder is used, as show in FIG. 4. Here the sample holder itself is a thermocouple. This sample holder comprises a crucible 15 which is sealed or perforated at a base where granulate carbon is placed. Crucible 15 is provided with wires 17, 18 which are surrounded by ceramic pipes which are collected in a ceramic pipe 19, at the top of which is a suspension device 20. The crucible 15 and two of the wires 17 are of platinum, whereas one of the wires 18 is of platinum and rhodium. Temperature registration takes place at a point 16 at which the wire 18 of platinum and rhodium is fastened to the crucible 15. The wires are connected to a plug 21.

Both of the sample holders described above are shaped in such a way that the respective thermocouple is in direct contact with the carbon product during analysis. This causes temperature recording to be very accurate.

The invention will be further explained in the following by means of examples.

Gas is introduced into tube furnace 2, which is made of gold, via inlet 4 at the base of the tube furnace, and such gas is preheated to reaction temperature as it passes radial radiation shield 6 inside the tube furnace on the way towards the carbon sample. The introduction of gas is regulated by the processing unit 1. A sufficiently generous amount of gas is introduced so that a further increase in amount has no influence on the test result.

The analysis of the test result is carried out automatically by the processing unit 1 via dialogue boxes. The processing unit 1 changes from the introduction of one gas to another gas automatically. During the heating of the sample, inert atmosphere ($N_2$) is introduced. The processing unit 1 automatically closes an $N_2$ valve and opens a respective air or $CO_2$ valve. When the reaction has been completed, the processing unit automatically switches back to $N_2$ and the sample is cooled down. Standard conditions during analysis are:

Heating time: 60 minutes

Reaction time: 180 minutes

Cooling time: 30 minutes

Reaction temperature during $CO_2$ test: 960° C.

Reaction temperature during air test: 525° C.

The flow of gas through the furnace is 100 Nl/h of $CO_2$ and 200 Nl/h of air. However, these reaction conditions may be easily changed by the operator.

The weighing system in the apparatus has a reproducibility of 1 mg. The weight is recorded continuously (every 20 seconds under standard conditions). The high number of measurements, the good reproducibility of the weighing system and the advanced temperature control which is within ±1° of the desired temperature, ensure high precision results. The precision is better than ±1%. The results of the analysis are calculated by the processing unit 1.

In an apparatus consisting of eight tube furnaces 2, it is possible to analyze eight carbon samples in the course of 4.5 hours. The time required to prepare a carbon sample for analysis is 10 minutes. As mentioned above, the processing unit 1 controls the furnaces 2 automatically. The time required for an operator to be able to prepare the samples, fasten the samples in the furnaces, remove the samples from the furnaces, collect the soot and read off the results for samples in eight furnaces is a total of 100 minutes.

Samples of different carbon anode materials were analyzed taking into account air reactivity, $CO_2$ reactivity and soot index. Standard procedures as indicated above were used during the tests. When air reactivity at 525° C. had been completely analyzed, the furnace temperature was automatically increased to 960° C. for analysis of $CO_2$ reactivity. For comparison, the anode samples were also analyzed in two separate tests in accordance with existing techniques, for $CO_2$ reactivity, air reactivity and soot index. The results from the reactivity measurements when using the procedure according to the present invention and when using existing techniques are shown in Table 1.

provide results in this case which are 1.5 times higher than the reactivity measurements from the existing technique. This is due to the fact that the carbon samples examined in accordance with the procedure of the present invention were pre-oxidized as they had already been investigated for air reactivity. The results achieved by using the method in accordance with the present invention for $CO_2$ reactivity and soot index are therefore probably more closely related to the realistic conditions in an electrolysis cell. The correlation coefficient is good (0.96).

Figure 7:
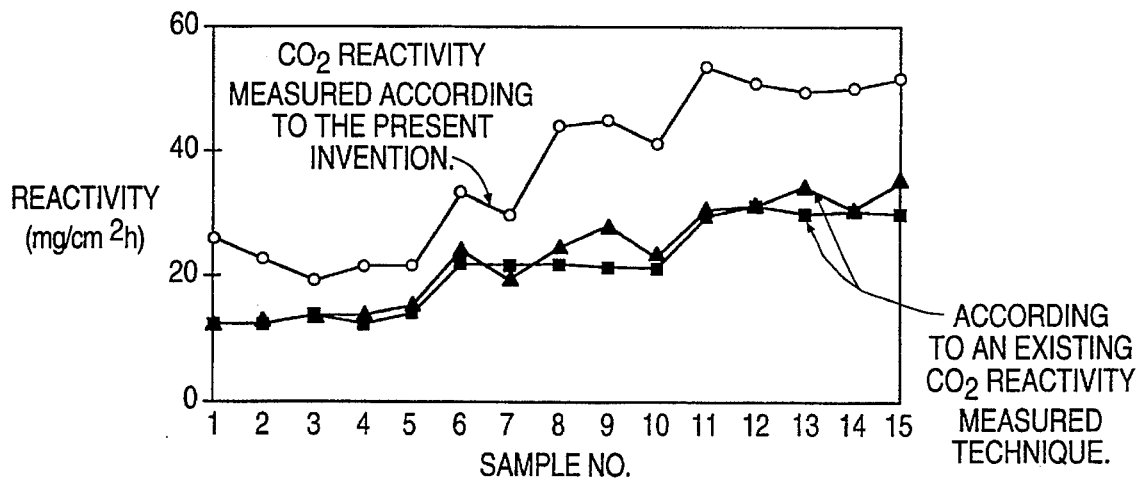
FIGS. 7 and 8 are graphs respectively illustrating results of individual $CO_2$ reactivity and soot index measurements.
Figure 8:
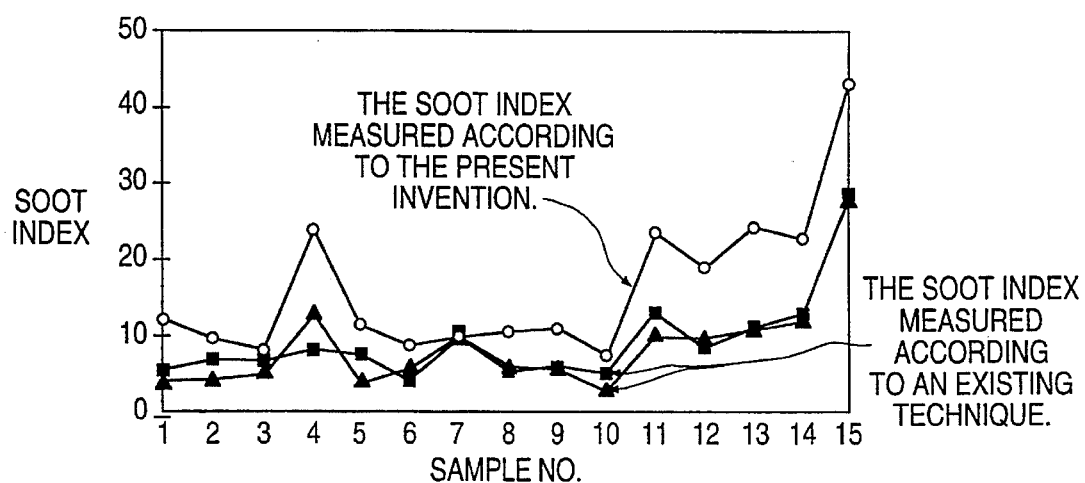

In FIGS. 7 and 8 the results from $CO_2$ reactivity and soot index measurements are plotted for each individual sample.

We claim:

1. A method of determining air reactivity, $CO_2$ reactivity and soot index of a carbon product, said method comprising:

first conducting an air reactivity analysis on a sample of said carbon product and thereby determining said air reactivity thereof;

after completion of said air reactivity analysis, then conducting a $CO_2$ reactivity analysis on said air reacted sample of said carbon product and thereby determining said $CO_2$ reactivity thereof; and after completion of said $CO_2$ reactivity analysis, collecting and weighing soot dust from said sample resulting from said analyses and thereby determining said soot index of said carbon product.

2. A method as claimed in claim 1, comprising conducting said $CO_2$ reactivity analysis at 960° C.

3. A method as claimed in claim 1, comprising conducting said air reactivity analysis at 525° C.

4. A method as claimed in claim 3, comprising conducting said $CO_2$ reactivity analysis at 960° C.

5. A method as claimed in claim 1, wherein said sample is within the interior of a tube furnace, and said conducting said air and $CO_2$ reactivity analyses comprise introducing an inert gas into said interior while heating said sample to an air

TABLE 1

| | Results from reactivity measurements | | | | | | | |
|---|---|---|---|---|---|---|---|---|
| | Test | | | Ref. test | | | Ref. test | |
| No. | Reac. $CO_2$ mg/cm²h | Soot index % | Reac. air mg/cm²h | Reac. $CO_2$ mg/cm²h | Soot index % | Reac. air mg/cm²h | Reac. $CO_2$ mg/cm²h | Soot index % |
| 1 | 26.2 | 12.3 | 20.4 | 12.4 | 4.2 | 27.1 | 12.5 | 5.5 |
| 2 | 22.6 | 9.8 | 18.3 | 12.4 | 4.7 | 18.4 | 12.0 | 6.9 |
| 3 | 19.1 | 7.6 | 17.0 | 13.5 | 5.3 | 18.8 | 13.1 | 6.0 |
| 4 | 21.3 | 23.7 | 20.4 | 13.5 | 12.7 | 24.5 | 12.2 | 7.9 |
| 5 | 21.8 | 11.7 | 18.4 | 15.0 | 4.1 | 19.1 | 14.2 | 7.4 |
| 6 | 33.4 | 8.4 | 19.3 | 24.1 | 5.9 | 21.7 | 22.0 | 4.3 |
| 7 | 29.9 | 9.9 | 21.7 | 19.7 | 10.0 | 20.6 | 21.3 | 10.5 |
| 8 | 44.2 | 10.8 | 23.3 | 25.1 | 6.0 | 24.0 | 22.0 | 5.3 |
| 9 | 44.8 | 11.1 | 24.4 | 28.7 | 6.3 | 25.7 | 21.2 | 6.1 |
| 10 | 40.8 | 7.5 | 21.4 | 23.0 | 3.2 | 26.9 | 20.8 | 5.1 |
| 11 | 53.3 | 23.9 | 31.4 | 30.6 | 10.5 | 37.1 | 29.6 | 13.1 |
| 12 | 50.9 | 19.1 | 30.4 | 31.6 | 10.1 | 24.9 | 31.9 | 8.7 |
| 13 | 49.3 | 24.2 | 34.7 | 34.6 | 11.5 | 33.1 | 29.7 | 11.1 |
| 14 | 49.5 | 22.7 | 35.5 | 30.5 | 12.4 | 33.8 | 30.6 | 12.8 |
| 15 | 51.3 | 43.3 | 47.1 | 35.3 | 28.0 | 46.0 | 30.1 | 28.5 |

Figure 5:
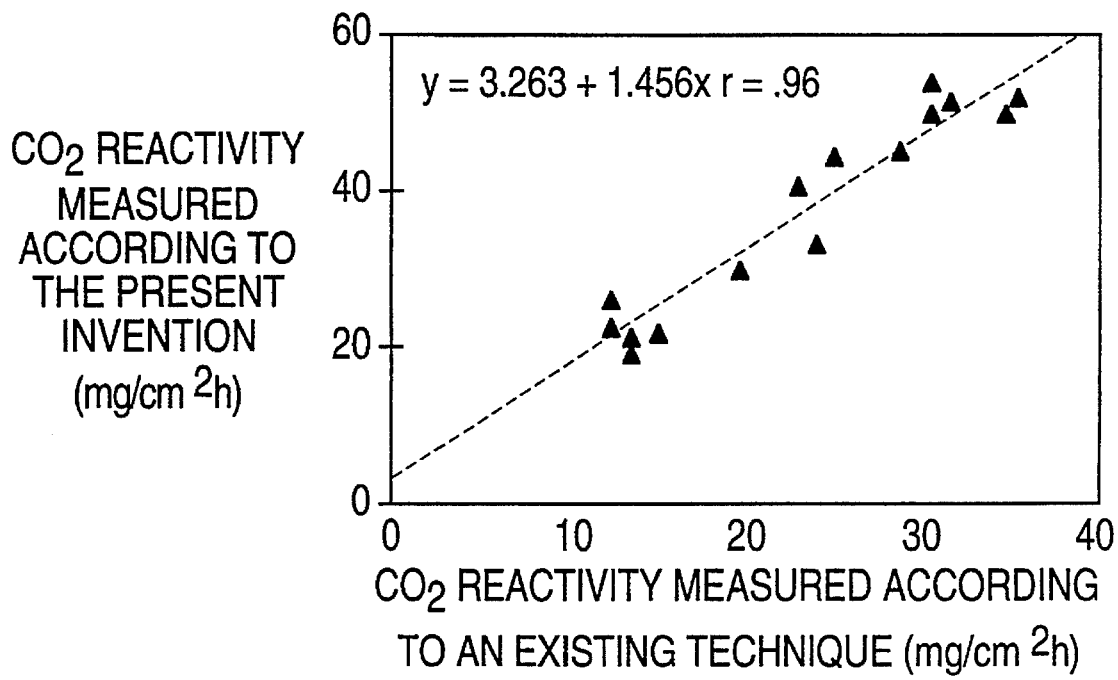
FIGS. 5 and 6 are graphs respectively illustrating measured $CO_2$ reactivity and soot index measurements in accordance with the method of the present invention as a function of corresponding measurements according to known techniques.
Figure 6:
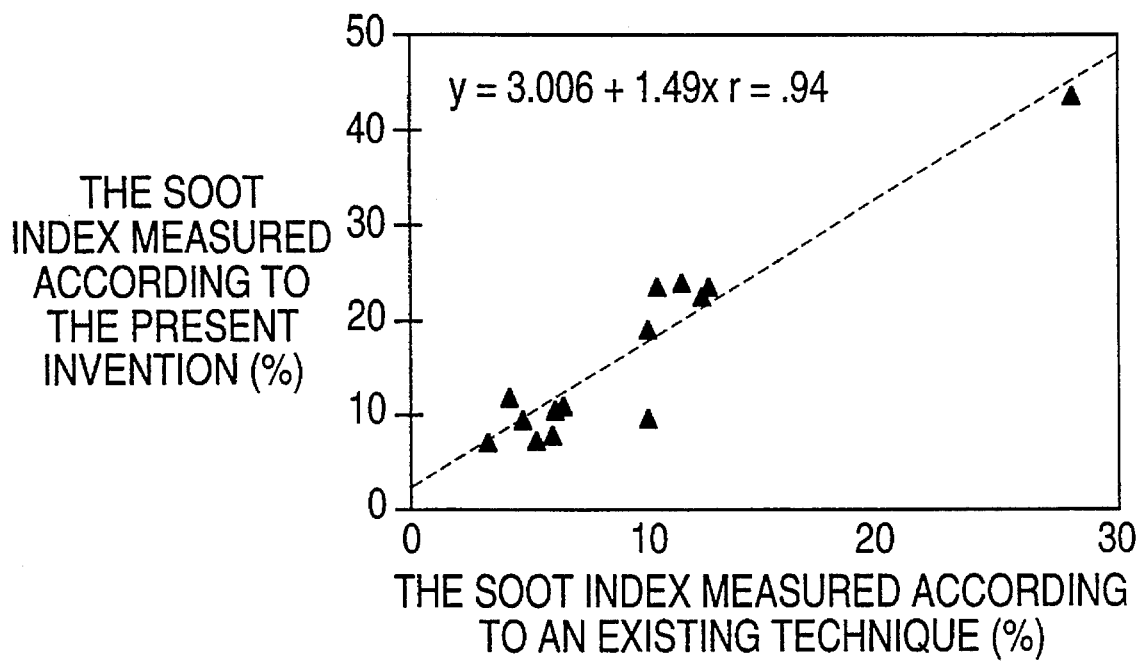

FIGS. 5 and 6 respectively show $CO_2$ reactivity and soot index analyzed in accordance with the procedure in the present invention as a function of the measurement by an existing technique. FIG. 5 shows that there is good correspondence between the results for the reactivity analyzed by means of the invention and the existing technique. The measurements in accordance with the present invention reactivity analysis temperature; when said sample has reached said air reactivity analysis temperature stopping said heating, interrupting said inert gas introduction, introducing air into said interior, and performing analysis of air reactivity of said sample; upon completion of said air reactivity analysis introducing further inert gas into said interior while further heating said sample from said air reactivity analysis temperature to a $CO_2$ reactivity analysis temperature; and when said sample has reached said $CO_2$ reactivity analysis temperature stopping said further heating, interrupting said further inert gas introduction, introducing $CO_2$ into said interior, and performing analysis of said $CO_2$ reactivity of said sample.

6. A method as claimed in claim 5 further comprising automatically performing and controlling all of the steps by a processing unit.

7. A method as claimed in claim 5, wherein said air reactivity analysis temperature is 525° C., and said $CO_2$ reactivity analysis temperature is 960° C.

* * * * *